US010414833B2

(12) United States Patent
Lim et al.

(10) Patent No.: US 10,414,833 B2
(45) Date of Patent: Sep. 17, 2019

(54) BIOCOMPATIBLE COMPOSITION AND METHOD FOR PREPARING SAME

(71) Applicant: INNO PHARM CO., LTD., Changwon-si, Gyeongsangnam-do (KR)

(72) Inventors: Jae Young Lim, Changwon-si (KR); Byoung-Chull Chung, Changwon-si (KR)

(73) Assignee: INNO PHARM CO., LTD., Changwon-si, Gyeongsangnam-Do (KR)

( * ) Notice: Subject to any disclaimer, the term of this patent is extended or adjusted under 35 U.S.C. 154(b) by 0 days.

(21) Appl. No.: 15/531,837

(22) PCT Filed: Jun. 23, 2015

(86) PCT No.: PCT/KR2015/006373
§ 371 (c)(1),
(2) Date: May 31, 2017

(87) PCT Pub. No.: WO2016/093451
PCT Pub. Date: Jun. 16, 2016

(65) Prior Publication Data
US 2017/0335021 A1 Nov. 23, 2017

(30) Foreign Application Priority Data
Dec. 8, 2014 (KR) .................. 10-2014-0175217

(51) Int. Cl.
A61K 8/73 (2006.01)
A61K 9/00 (2006.01)
C08L 5/08 (2006.01)
C08B 37/00 (2006.01)
C08B 37/08 (2006.01)
A61L 27/20 (2006.01)
A61L 27/26 (2006.01)
A61L 27/50 (2006.01)
A61L 27/58 (2006.01)
G01N 11/00 (2006.01)

(52) U.S. Cl.
CPC ............ C08B 37/0072 (2013.01); A61K 8/73 (2013.01); A61K 9/00 (2013.01); A61L 27/20 (2013.01); A61L 27/26 (2013.01); A61L 27/50 (2013.01); A61L 27/58 (2013.01); C08B 37/0024 (2013.01); A61L 2400/06 (2013.01); G01N 11/00 (2013.01)

(58) Field of Classification Search
None
See application file for complete search history.

(56) References Cited

U.S. PATENT DOCUMENTS

| 4,582,865 A | 4/1986 | Balazs et al. |
| 6,387,413 B1 | 5/2002 | Miyata et al. |
| 6,703,444 B2 * | 3/2004 | Zhao ............... A61K 8/735 424/423 |
| 2011/0275795 A1 * | 11/2011 | Song ............... A61L 27/20 536/123.12 |
| 2013/0196944 A1 | 8/2013 | Barg |
| 2013/0224277 A1 * | 8/2013 | Amedee ........... A61L 27/20 424/423 |
| 2014/0315828 A1 | 10/2014 | Pavlovic et al. |

FOREIGN PATENT DOCUMENTS

| CA | 2371543 A1 | 11/2000 |
| CN | 102911380 A | 2/2013 |
| DE | 19920557 A1 | 11/2000 |
| KR | 20000055724 A | 9/2000 |
| KR | 100374666 B1 | 3/2003 |
| KR | 20070073507 A | 7/2007 |
| KR | 20130015427 A | 2/2013 |
| KR | 20140094295 A | 7/2014 |
| WO | 2012053776 A9 | 4/2012 |
| WO | 2013036568 A1 | 3/2013 |

OTHER PUBLICATIONS

Lee, Macromolecular Research, vol. 11, No. 5, pp. 368-374 (2003). (Year: 2003).*
Mayell, Alternative Medicine Review, vol. 6, No. 1, 2000. (Year: 2000).*
De Marco, Chemical Engineering Transactions, vol. 38, 2014. (Year: 2014).*
The extended European search report, 15867154.5, dated Jun. 29, 2018.
XP-002781996, WPI/2017 Clarivate Analytics.
Miura et al., "Blood clearance of (1→3)-beta-D-glucan in MRL lpr/lpr mice", FEMS Immunology and Medical Microbiology, 1996, vol. 13, Issue 1, Abstract only.
Pillai et al., "Anti-Wrinkle Therapy: Significant New Findings in the Non-Invasive Cosmetic Treatment of Skin Wrinkles with Beta-Glucan", International Journal of Cosmetic Science, 2005, vol. 27, Issue 5, Abstract only.
International Search Report for International Application No. PCT/KR2015/006373 (dated Sep. 14, 2015) (7 Pages).
Anno, Kimiko et al., Basics of Sugar Chemistry, Aug. 10, 1995, pp. 129-133.
Harada, Tokuya, General Polysaccharides Science, Dec. 1, 1974, p. 202.

* cited by examiner

Primary Examiner — Layla D Berry
(74) Attorney, Agent, or Firm — Lucas & Mercanti, LLP

(57) ABSTRACT

The present disclosure relates to a biocompatible composition and a method for preparing the same, and a hybrid composition of β-glucan and hyaluronic acid is prepared by hybrid cross-linkage. The biocompatible composition of the present disclosure high stability against heat and bio-enzymes, and thus is capable of being used as a medical material.

2 Claims, 3 Drawing Sheets

[FIG 1]
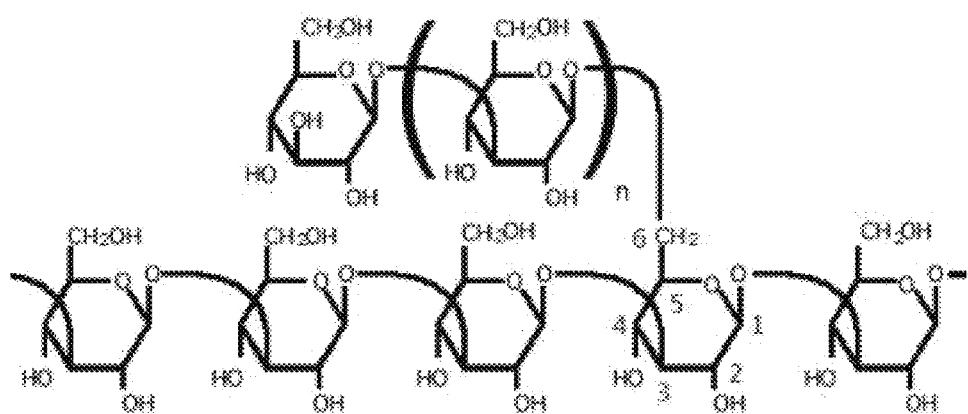

[FIG 2]

[FIG 3]
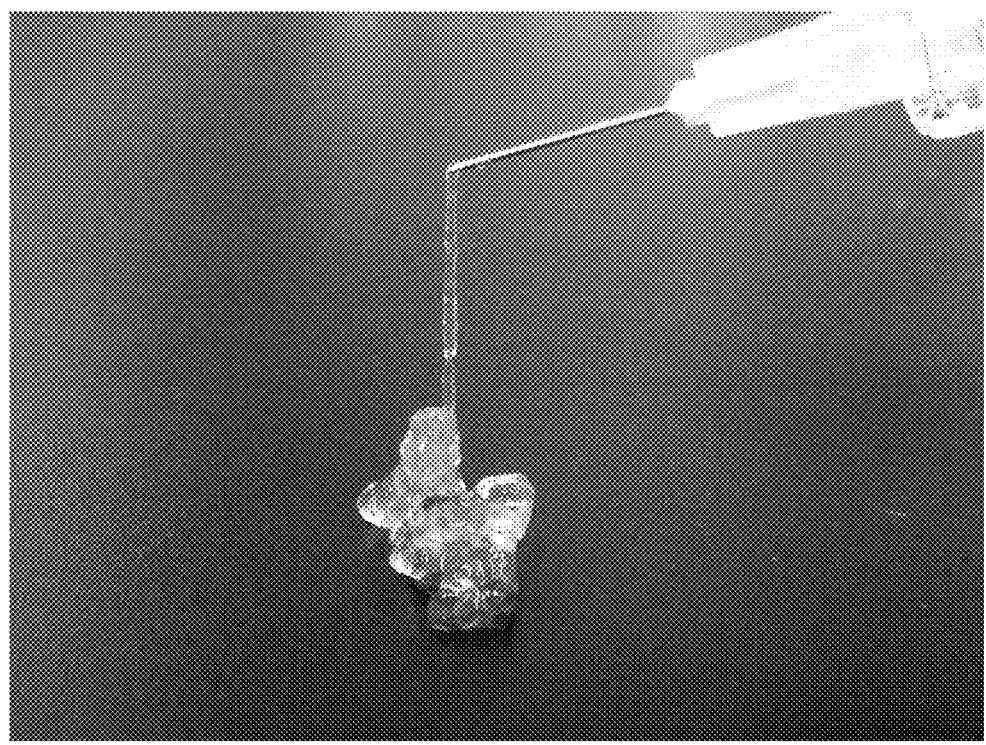

BIOCOMPATIBLE COMPOSITION AND METHOD FOR PREPARING SAME

CROSS-REFERENCE TO RELATED APPLICATIONS

This application is a 371 of PCT/KR2015/006373, filed on Jun. 23, 2015, which claims the benefit of Korean Patent Application No. 10-2014-0175217 filed Dec. 8, 2014 the contents of each of which are incorporated herein by reference.

TECHNICAL FIELD

The present disclosure relates to a biocompatible composition and a method for preparing the same, and in particular, to a biocompatible composition usable in medical products, cosmetics and the like inserted into the human body or in contact with the skin, and a method for preparing the same.

BACKGROUND ART

Materials of medical instruments and prostheses inserted into the human body are in direct contact with blood, tissue, organs and the like, and need to be accompanied with stability, and such materials are referred to as biocompatible materials. Various preparation methods have been studied in order to develop biocompatible materials. Particularly, development of new materials by crosslinking biocompatible materials that have been developed in the art to supplement individual properties of these materials has been accelerated.

Hyaluronic acid and derivatives thereof have high viscosity, excellent biocompatibility and complete biodegradability, and have been used in a wide range of applications.

However, hyaluronic acid and derivatives thereof are readily degraded by heat and bio-enzymes (hyaluronidase and the like) losing an inherent nature of hyaluronic acid. In prostheses inserted into the living body, fast biodegradability and loss of an inherent nature make a cycle of prosthesis insertion into the human body short, and become a factor impairing performance as prostheses by decreasing viscosity and elasticity. For example, general hyaluronic acid fillers have retention length of 6 months to 1 year in the living body, however, original viscosity and elasticity are readily lost within the period causing a problem.

As a result, hyaluronic acid and derivatives thereof secure biocompatibility, but need to supplement disadvantages of shortening a remodeling procedure cycle of fillers and the like. In addition, when prostheses and the like are degraded inside the living body, the degraded products should not adversely affect the human body and need to bring advantageous effects.

DISCLOSURE

Technical Problem

The present disclosure is directed to providing a biocompatible composition completely degraded by heat and bio-enzymes, but maintaining original viscosity and elasticity without being readily degraded in a short period of time, and a method for preparing the same.

Technical Solution

The present disclosure has been made in view of the above, and a biocompatible composition according to one embodiment of the present disclosure is a hybrid-crosslinked material of β-glucan and hyaluronic acid. The β-glucan may be formed with plant-derived β-(1,3)-glucan, β-(1,4)-glucan, β-(1,6)-glucan, or a mixture of at least two or more of these, and β-(1,6) glucan having a side chain in β-(1,3) is preferably used.

As the β-glucan, those having a molecular weight of 30,000 Da to 300,000 Da are preferably used, and those derived from *Grifola frondosa* mycelium may be used.

A method for preparing a biocompatible composition according to one embodiment of the present disclosure includes (a) mixing β-glucan having a molecular weight of 30,000 Da to 300,000 Da and hyaluronic acid, and (b) adding a crosslinking agent including at least one of an epoxide group, an epihalohydrin group and a divinylsulfonyl group. The β-glucan and the hyaluronic acid in the (a) step may be mixed in a mass ratio of 1:9 to 9:1. The crosslinking agent of the (b) step may be selected from the group consisting of 1,4-butandiol diglycidyl ether (BDDE), ethylene glycol diglycidyl ether (EGDGE), 1-(2,3-epoxypropyl)-2,3-epoxycyclohexane, 1,2-ethandiol diglycidyl ether and mixtures thereof.

Advantageous Effects

A biocompatible composition according to the present disclosure is a new material in which hyaluronic acid and β-glucan are crosslinked, and is capable of maintaining original form and properties in the human body due to high stability against heat and bio-enzymes, and is effective in facilitating collagen synthesis after biodegradation.

DESCRIPTION OF DRAWINGS

FIG. 1 is a chemical formula of β-(1,6) glucan having a side chain in β-(1,3) according to one embodiment of the present disclosure.

FIG. 2 is an image of a biocompatible composition of the present disclosure being swollen in a physiological saline solution.

FIG. 3 is an image of a biocompatible composition of the present disclosure being extruded through an injection needle.

MODE FOR DISCLOSURE

Detailed descriptions of the present disclosure provided below are described as specific embodiments that may implement the present disclosure and are provided in detail so as to be sufficient for those skilled in the art to implement the present disclosure. Various embodiments of the present disclosure need to be construed as being different from each other but are not necessarily mutually exclusive. Accordingly, detailed descriptions provided below is not implemented as limitative meaning, and the scope of the present disclosure needs to be accepted as to include contents described in the claims and a full range equivalent thereto.

A biocompatible composition according to one embodiment of the present disclosure has a form of β-glucan and hyaluronic acid being hybrid-crosslinked. Materials usable for preparing the biocompatible composition of the present disclosure will be described first.

<β-Glucan>

β-glucan usable for preparing the biocompatible composition of the present disclosure has a form of a polymer in which glucose monomers are linked through glycosidic bonds. β-glucan may be derived from natural plants. For example, β-glucan may be extracted and derived from fungi, yeast cellular walls, grains and the like. However, β-glucan usable for preparing the biocompatible composition of the present disclosure may be derived through chemical syntheses and polymerization as well as from natural plants. As preferred embodiments, β-glucan may be extracted and used from a *Grifola frondosa* mycelium culture medium having high β-glucan content and a relatively shorter mycelium culture period compared to other fungi.

Effects of β-glucan in the increase of immunity for the living bodies have been already reported (FEMS immunology and medical microbiology, 13 (1): 51-57; Vetvicka, V et al, (1996)). β-glucan is sold as pharmaceuticals or functional foods for anticancer in Japan, and FDA of the US has established safety criteria for β-glucan and certified its effects in the increase of immunity and its stability. In addition, in skin care-relating industries, β-glucan is used as a raw material of cosmetics for enhancing viscoelasticity, moisturizing properties, biocompatibility, collagen synthesis facilitating effects, and skin regeneration and protection effect (Journal of Cosmetic Science, 27(5): 292).

β-glucan is divided into β-(1,3)-glucan, β-(1,4)-glucan and β-(1,6)-glucan depending on the position of glucose monomers being linked. The β-glucan usable in the present disclosure includes β-(1,3)-glucan, β-(1,4)-glucan, β-(1,6)-glucan or a mixture of at least two or more of these, and also includes β-(1,3)-glucan, β-(1,4)-glucan or β-(1,6)-glucan each having a side chain. Particularly, β-(1,6)-glucan having a side chain in β-(1,3) is preferably used among the above-mentioned β-glucans. FIG. 1 is a chemical formula of β-(1,6)-glucan having a side chain in β-(1,3).

Preparing the β-glucan by segmenting β-glucan having a molecular weight of 30,000 Da to 300,000 Da is preferred in enhancing viscosity, swelling property and syringe extrusion.

<Hyaluronic Acid>

Hyaluronic acid is one of polysaccharides formed with amino acid and uronic acid, and is a polymer compound formed with N-acetylglucosamine and glucuronic acid. Hyaluronic acid usable in the present disclosure has a molecular weight of 100,000 Da to 1,000,000 Da. Hyaluronic acid used in embodiments of the present disclosure has a molecular weight of 150,000 Da to 300,000 Da, and a product of Sigma-Aldrich Co. LLC. is purchased and used.

<Preparation of Biocompatible Composition>

A method for preparing a biocompatible composition of the present disclosure includes (a-1) preparing an aqueous solution by diluting β-glucan in an aqueous basic solution, (a-2) adjusting a pH of the aqueous solution to 9 to 13, (a-3) hydrolyzing the β-glucan to low molecular β-glucan (30,000 Da to 300,000 Da) by applying hydrogen peroxide and heat under a basic condition, (a-4) separating the low molecular weight β-glucan, (a-5) mixing the aqueous β-glucan solution and hyaluronic acid in a mass ratio of 1:9 to 9:1, (b) adding a crosslinking agent, and (c) progressing a crosslinking reaction for 2 hours to 8 hours at 25° C. to 80° C.

Specifically, β-glucan from natural plants is dissolved in an aqueous basic solution and then homogenized (a-1). The aqueous basic solution includes an aqueous sodium hydroxide solution, an aqueous sodium bicarbonate solution, an aqueous calcium hydroxide solution, an aqueous barium hydroxide solution, an aqueous aluminum hydroxide solution, and ammonia water. Preferably, an aqueous sodium hydroxide solution is used to adjust the pH to from 9 to 13 (a-2). Subsequently, hydrogen peroxide is added in 0.5% to 1.5% (v/v) thereto, and the result is hydrolyzed for 10 minutes to 90 minutes under a condition of a temperature of 100° C. to 180° C. and an atmosphere of 1 to 2 (a-3).

The hydrolyzed β-glucan may have various molecular weights. Using a filtering equipment, β-glucan having a molecular weight of 30,000 Da to 300,000 Da is separated from the hydrolyzed β-glucan (a-4). Next, the separated β-glucan is freeze-dried.

The freeze-dried β-glucan is dissolved in an aqueous basic solution, and then homogenized. Subsequently, hyaluronic acid is mixed thereto (a-5). Herein, the β-glucan and the hyaluronic acid are preferably mixed in a mass ratio of 1:9 to 9:1.

Subsequently, a crosslinking agent is added thereto (b). The crosslinking agent may include at least one of an epoxide group, an epihalohydrin group and a divinylsulfonyl group. For example, the epoxide group may be selected from the group consisting of 1,4-butanediol diglycidyl ether (BDDE), ethylene glycol diglycidyl ether (EGDGE), 1-(2, 3-epoxypropyl)-2,3-epoxycyclohexane, 1,2-ethandiol diglycidyl ether and mixtures thereof. Among these, 1,4-butandiol diglycidyl ether having proven stability and having less inflammation or allergy reactions compared to other crosslinking agents is preferably used, and the crosslinking agent may be added in 0.1% to 5.0% (v/v) with respect to the total volume of the β-glucan and hyaluronic acid mixture prior to the crosslinking agent addition.

Subsequently, a hybrid crosslinking reaction is progressed for 2 hours to 8 hours at 25° C. to 80° C. (c). When the crosslinking reaction is terminated, the result is neutralized to a physiological pH (7.4) using hydrochloric acid, and washed to be freeze-dried.

Using the preparation method described above, the biocompatible composition of the present disclosure may be prepared. The biocompatible composition of the present disclosure may be diversely used as surgical instruments, prostheses, fillers, cosmeceutical materials and the like inserted into the human body.

Hereinafter, the method for preparing a biocompatible composition of the present disclosure will be described in more detail with reference to examples of the present disclosure, however, the present disclosure is not limited to these examples.

EXAMPLE

1. Preparation and Hydrolysis of Aqueous β-Glucan Solution

β-glucan extracted from *Grifola frondosa* was obtained. The β-glucan is β-(1,6) glucan having a side chain in β-(1,3). 20 g of the β-glucan powder was dissolved in 100 ml of a 1.0% sodium hydroxide solution and homogenized until a transparent solution was obtained, and then hydrogen peroxide was added in 1.0% (v/v) thereto. After that, the β-glucan was hydrolyzed through high temperature and high pressure (121° C. and 1.2 atmosphere) treatment for 60 minutes at 121° C. The hydrolyzed β-glucan was segmented by molecular weights using an ultrafiltration apparatus and then freeze-dried, and the results are shown in Table 1.

TABLE 1

| Molecular Weight | Before Hydrolysis | After Hydrolysis |
|---|---|---|
| 300,000 Da or greater | 18.9 g | 4.2 g |

TABLE 1-continued

| Molecular Weight | Before Hydrolysis | After Hydrolysis |
|---|---|---|
| 100,000 Da to 300,000 Da | — | 2.6 g |
| 30,000 Da to 100,000 Da | — | 6.2 g |
| Loss (g) | 1.1 g | 7.0 g |

2. Preparation of Hybrid Crosslinked Composition 4 g of the low molecular β-glucan powder of 30,000 Da to 300,000 Da was dissolved in 100 ml of a 1.0% sodium hydroxide solution, and homogenized until a transparent solution was obtained. After preparing a 4.0% (w/v) aqueous hyaluronic acid solution, the solution was added to the aqueous low molecular β-glucan solution, and the result was homogeneously mixed through stirring. 0.3% (v/v) of 1,4-butanediol diglycidyl ether (BDDE) was added thereto with respect to the total volume of the obtained β-glucan and hyaluronic acid mixture, and then a crosslinking reaction was progressed for 6 hours at 60° C. After the crosslinking reaction was terminated, the pH was neutralized to a physiological pH (7.4) by adding 5 N hydrochloric acid (HCl). The prepared hybrid crosslinked composition was washed 3 to 4 times with ethanol and then freeze-dried.

Test Example 1

Degree of Swelling

Results of measuring a degree of swelling for the biocompatible composition prepared in the example (Example) and a degree of swelling for low molecular weight β-glucan with no hyaluronic acid cross-linkage thereto (Comparative Example) are shown in Table 2. After freeze-drying Example, the weight of the biocompatible composition measured (dried weight, Wd) and the weight measured after being swollen in a physiological saline solution for 24 hours and then removing surface moisture (swollen weight, Ws) were calculated using the following formula.

[Degree of Swelling=(Ws−Wd)/Wd]

TABLE 2

| Category | Swollen Weight (Ws) | Dried Weight (Wd) | Degree of Swelling (Ws-Wd)/Wd |
|---|---|---|---|
| Comparative Example | — | 0.34 g | Dissolved (Impossible to Measure) |
| Example | 8.18 g | 0.34 g | 23.06 |

FIG. 2 is an image of the biocompatible composition being swollen in a physiological saline solution in Test Example 1.

Test Example 2

Syringe Extrusion

In order to measure extruded force of the swollen biocompatible composition of Test Example 1, a 1 cc syringe was filled with the composition and whether the composition was extruded through a 27 G×1/2" injection needle was measured.

FIG. 3 is an image of the biocompatible composition of the present disclosure being extruded through an injection needle. As shown in FIG. 3, the hybrid crosslinked composition of low molecular β-glucan of 30,000 Da to 300,000 Da and hyaluronic acid according to the present disclosure was readily extruded through a 27 G injection needle, and also exhibited excellent viscoelasticity.

Test Example 3

Stability Against Heat

In order to compare and measure stability against thermal degradation of the biocompatible composition of the present disclosure (Example) and commercial crosslinked hyaluronic acid (Comparative Example), these were high temperature and high pressure treated for 60 minutes at 121° C., and each viscosity thereof was compared before and after sterilization. The viscosity was measured using a Brookfield Rheometer, and the results are shown in Table 3. The crosslinked hyaluronic acid of Comparative Example was prepared by preparing a 4.0% (w/v) aqueous hyaluronic acid solution using hyaluronic acid having a molecular weight of 150,000 Da to 300,000 Da purchased from Sigma-Aldrich Co. LLC., then adding 0.3% (v/v) of 1,4-butanediol diglycidyl ether (BDDE) thereto with respect to the total volume of the aqueous hyaluronic acid solution, and crosslinking the result for 6 hours at 60° C.

TABLE 3

| Category | Viscosity before Sterilization (cP) | Viscosity after Sterilization (cP) | Viscosity Decrease |
|---|---|---|---|
| Comparative Example | 942 | 645 | 31.5% |
| Example | 3164 | 2812 | 11.1% |

As shown in Table 3, it was seen that the biocompatible composition of the present disclosure had excellent stability against thermal degradation compared to Comparative Example.

Test Example 4

Stability Against Enzyme Degradation

Stability of the 1.0% aqueous hyaluronic acid solution (Comparative Example) and the biocompatible composition (Example) against hyaluronidase enzyme was compared and investigated. 1,500 IU of hyaluronidase enzyme was added to each of Example and Comparative Example, the result was reacted for 30 minutes at 37° C., and viscosity was measured using a Brookfield Rheometer, and measurement results are shown in Table 4.

TABLE 4

| Category | Viscosity before Enzyme Reaction (cP) | Viscosity after Enzyme Reaction (cP) | Viscosity Decrease |
|---|---|---|---|
| Comparative Example | 450 | 281 | 37.6% |
| Example | 1525 | 1410 | 7.5% |

As shown in Table 4, it was seen that the biocompatible composition of the present disclosure had more superior stability against bio-enzyme degradation compared to Comparative Example.

The present disclosure relates to a method for preparing a biocompatible composition, and a biocompatible composition prepared using the method, and the composition is capable of being used as medical and cosmeceutical materials such as prostheses and fillers for human body insertion.

The invention claimed is:

1. A biocompatible dermal filler composition in which β-glucan and hyaluronic acid are crosslinked to each other with a crosslinking agent selected from the group consisting of 1,4-butandiol diglycidyl ether (BDDE), ethylene glycol diglycidyl ether (EGDGE), 1-(2,3-epoxypropyl)-2,3-epoxy-cyclohexane, 1,2-ethandiol diglycidyl ether and mixtures thereof,
   wherein the β-glucan is derived from *Grifola frondosa* mycelium and has a molecular weight of 30,000 Da to 300,000 Da.

2. The biocompatible dermal filler composition of claim 1, wherein the biocompatible composition is prepared by mixing the β-glucan and the hyaluronic acid in a mass ratio of 1:9 to 9:1.

* * * * *